(12) United States Patent
Van Dijk et al.

(10) Patent No.: US 8,742,384 B2
(45) Date of Patent: Jun. 3, 2014

(54) OPTICAL ILLUMINATION APPARATUS AND METHOD HAVING A REFLECTIVE ARRANGEMENT WITH MOVEABLE COMPONENTS FOR ADJUSTING INCIDENT LIGHT

(75) Inventors: Erik Martinus Hubertus Petrus Van Dijk, Eindhoven (NL); Cornelius Antonius Hezemans, Neunen (NL)

(73) Assignee: Koninklijke Philips N.V., Eindhoven (NL)

( * ) Notice: Subject to any disclaimer, the term of this patent is extended or adjusted under 35 U.S.C. 154(b) by 310 days.

(21) Appl. No.: 12/992,608

(22) PCT Filed: May 18, 2009

(86) PCT No.: PCT/IB2009/052055
§ 371 (c)(1),
(2), (4) Date: Nov. 15, 2010

(87) PCT Pub. No.: WO2009/144614
PCT Pub. Date: Dec. 3, 2009

(65) Prior Publication Data
US 2011/0068260 A1    Mar. 24, 2011

(30) Foreign Application Priority Data

May 26, 2008   (EP) ..................................... 08156878

(51) Int. Cl.
*G01N 21/86*    (2006.01)
(52) U.S. Cl.
USPC ....................................... 250/559.4; 250/205

(58) Field of Classification Search
USPC ............... 250/201.3, 201.2, 201.4, 216, 221, 250/559.4, 235, 234, 458.1, 459.1, 205; 356/317, 318, 417, 418; 359/368–385
See application file for complete search history.

(56) References Cited

U.S. PATENT DOCUMENTS

| 5,459,325 A | 10/1995 | Hueton et al. |
| 6,762,840 B1 | 7/2004 | Kimura |
| 7,466,408 B2 * | 12/2008 | Tanaami ........................ 356/317 |
| 2002/0121611 A1 | 9/2002 | Yokokawa et al. |
| 2003/0095254 A1 | 5/2003 | Tanaami |
| 2004/0071394 A1 | 4/2004 | Gfrorer et al. |
| 2007/0076208 A1 | 4/2007 | Koo |

FOREIGN PATENT DOCUMENTS

| JP | 2001194303 A | 7/2001 |
| JP | 2004055071 A | 2/2004 |

* cited by examiner

*Primary Examiner* — Que T Le

(57) ABSTRACT

An optical system for detecting light from a 2D area of a sample (36) comprises a collection lens (34) for collecting light from a collection region of the sample. A light detector (44) is positionally fixed with respect to the sample, and a reflector arrangement (61) directs collected light to the detector. The reflector arrangement comprises movable components and the collection lens (34) is movable relative to the sample. The collection lens and the movable components are configurable to define different collection regions, and the movement of the components effects a direction of the light from the collection region to a substantially unchanged area of the light detector (44). This arrangement avoids the need for a bulky detector in order to detect signals from a 2D sample area formed by scanning across the sample.

15 Claims, 7 Drawing Sheets

OPTICAL ILLUMINATION APPARATUS AND METHOD HAVING A REFLECTIVE ARRANGEMENT WITH MOVEABLE COMPONENTS FOR ADJUSTING INCIDENT LIGHT

FIELD OF THE INVENTION

The invention relates to an optical illumination apparatus and method. For example, optical illumination is used in fluorescence detection systems and methods.

BACKGROUND OF THE INVENTION

An example of the use of fluorescence detection is in nucleic acid testing (NAT). This is a core element in molecular diagnostics for detecting genetic predispositions for diseases, for determining RNA expression levels or identification of pathogens, like bacteria and viruses that cause infections.

In many cases, particularly in the identification of pathogens, the amount of target DNA present in a reasonable sample volume is very low, and this does not allow direct detection. Amplification techniques are necessary to obtain detectable quantities of the target material. Different amplification techniques have been proposed and are used in daily practice. The most widely used are based on the so-called Polymerase chain reaction (PCR).

The amplification involves the denaturing of double-stranded DNA at elevated temperature (typically >90 degrees Celsius), specific binding of primers to the DNA sample at a reduced temperature (approximately 65 degrees) and copying of the original sequences starting from the primer position (at approximately 70 degrees). This procedure is repeated and in every cycle the amount of DNA with the specific sequence is doubled (when proceeding at 100% efficiency).

After amplification, the presence of target DNA is detected by measuring the fluorescence intensity of the labeled amplified DNA, for instance after electrophoretic separation in a capillary or after hybridization to so-called capture probes which are applied in spots on a surface over which the amplification product is flowed.

This invention relates to the apparatus used to provide the illumination to the sample, and the method of use.

The standard technique for fluorescence detection is the use of a scanning confocal microscope. Typically, a small (<1 μm), diffraction limited spot is used to excite the fluorescence in the focal plane. In the detection part of the system, only the light resulting from this single excitation point is detected.

It has previously been proposed that the excitation of a number of spots or a complete line in parallel enables an increase in the scanning speed, without a major impact on the confocality of the detection system. A pixilated detector can be used to detect the fluorescent emission.

The main disadvantage of a camera is the readout speed and the fact that these detectors are rather bulky and expensive. It is the aim of this invention to overcome these problems by sacrificing the spatial resolution along the length of the excitation line. A more compact solution is important for Point of Care test solutions.

SUMMARY OF THE INVENTION

According to the invention, there is provided an optical system for detecting light from a 2D area of a sample, comprising:

a collection lens for collecting light from a collection region of the sample;

a light detector which is in use positionally fixed with respect to the sample;

a reflector arrangement for directing collected light to the detector, wherein the reflector arrangement comprises movable components and the collection lens is movable relative to the sample, wherein the collection lens and the movable components are configurable to define different collection regions, and wherein the movement of the components effects a direction of the light from the collection region to a substantially unchanged area of the light detector.

This arrangement avoids the need for a bulky detector in order to detect signals from a 2D sample area formed by scanning across the sample. This enables a more compact, cheaper and simpler solution.

The reflector arrangement can comprise first and second reflectors which reflect the collected light in perpendicular planes, and a third reflector which directs the collected light output from the second reflector to the detector. The use of perpendicular planes of reflection means that one reflector can be moved linearly without affecting the position of the input and output beam for the other reflector. The first and second reflectors thus preferably comprise movable components, movable along the axis of the reflected collected light. The position of the light input to and output from the third reflector is then static, so that a small static detector can be used.

The system may further comprise an illumination system for illuminating the sample, the illumination system comprising:

a light source and an arrangement for directing the light source output to the reflector arrangement, wherein the reflector arrangement directs the light source output to the sample.

The same reflector arrangement is thus used for illuminating a sample and for collecting light from the sample, for example excitation light generated in response to the illumination.

The reflector arrangement again can comprise the first and second reflectors which reflect the collected light in perpendicular planes and the third reflector which directs the collected light output from the second reflector to the detector. In addition, a wavelength dependent reflector can be provided. This arrangement can define:

a first, collection light path between the sample and the detector comprises transmission through the wavelength dependent reflector, reflection at the first reflector, reflection at the second reflector and reflection at the third reflector; and a second, light source light path between an input to the reflector arrangement and the sample comprises reflection at the second reflector, and reflection at the wavelength dependent reflector.

These two paths provide routing of excitation light to the sample, and collection of light, with wavelength selectivity between the paths. The second path preferably misses the third reflector and the first reflector.

The reflector arrangement can further comprise a cylindrical lens only in the second, light source path. This enables line-shaped illumination to be used to illuminate the sample.

The system can comprise a fluorescence detection system, wherein the illumination system is for excitation of the sample to generate fluorescence. The collection region can then comprise a line with diffraction limited width.

The light sensitive area of the detector is preferably matched to the size and shape of the illumination provided to the detector by the reflector arrangement. For example, the detector can comprise a single light sensitive area, for example a photodiode. The detector may further comprise an imaging lens which focuses onto the detection surface.

The invention also provides a method of collecting light from a sample, comprising:

scanning a collection lens to collect light from a succession of collection regions of the sample;

using a reflector arrangement to directing collected light to a detector, wherein the reflector arrangement comprises movable components and the collection lens is movable relative to the sample, wherein the method comprises configuring the collection lens and the movable components to define the different collection regions, and wherein the movement of the components effects a direction of the light from the collection region to a substantially unchanged area of the light detector.

The invention also provides a method of measuring the fluorescence from a sample, comprising:

scanning an optical signal across the sample thereby providing excitation radiation to the collection regions; and collecting light emitted from the analysis region of the sample by excitation-induced fluorescence using the collection method of the invention; and detecting the collected light.

BRIEF DESCRIPTION OF THE DRAWINGS

Examples of the invention will now be described in detail with reference to the accompanying drawings, in which.

DETAILED DESCRIPTION OF THE EMBODIMENTS

Generally, the invention relates to an optical system for collecting light from a sample. A reflector arrangement directs the collected light to a detector, and is configurable to define different collection regions on the sample. Movement of the components of the reflector arrangement effects a direction of the light from the collection region to a substantially unchanged area of the light detector.

The system can be used for exciting fluorescence in a sample, for subsequent detection as part of a bio sensing procedure.

Methods are known for the detecting fluorophores in a device by exciting the fluorophores by light radiation through an objective lens and collecting the luminescence, for example through the same lens in a reflective mode. The luminescent radiation is projected onto a sensor device after having passed a filter device to select the appropriate wavelength range. The lens can be moved in a controlled way in three directions by different actuation means, to enable scanning over a sample of interest. A confocal imaging arrangement is typically used.

Figure 1:
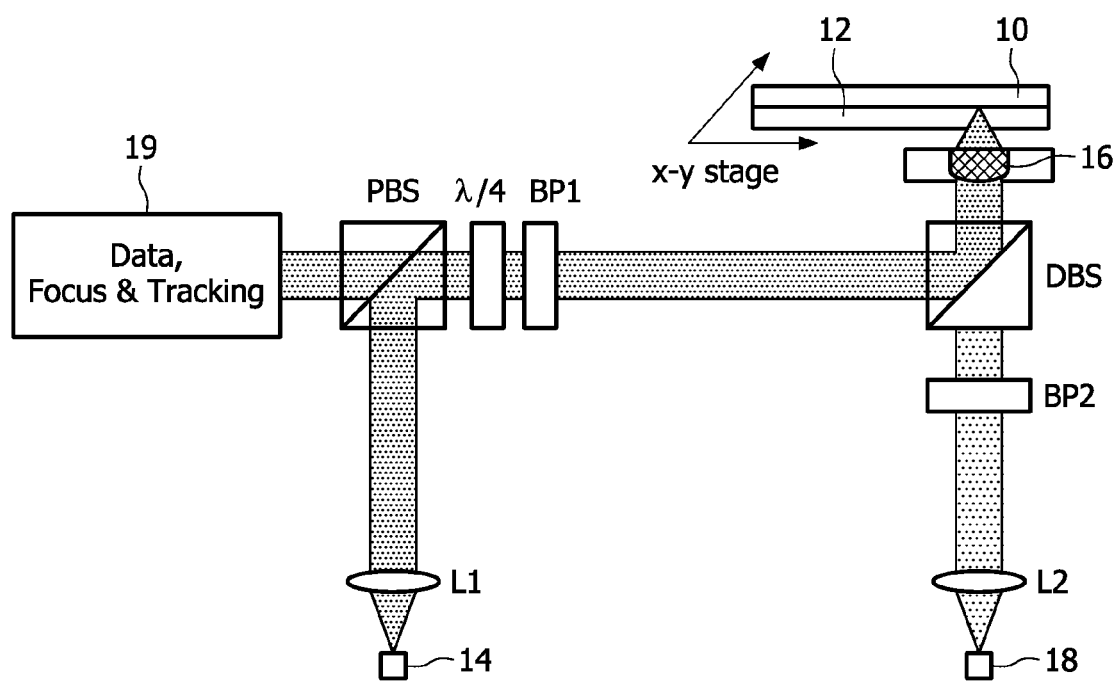
FIG. 1 shows a known fluorescence scanner based on a DVD optics system.

FIG. 1 shows the basic components of a known fluorescence scanner based on a DVD optical system. The sample to be investigated is confined into a given volume forming a micro-fluidic part 10 by a substrate 12. The light generated by a light source 14 such as a laser is used to excite fluorescence. The light is collimated by a collimator lens L1 and subsequently focused in the sample by means of an excitation lens 16.

The lens 16 can move relative to the sample, preferably in all three dimensions. This relative motion can be decoupled arbitrarily, for example the sample can move in to the x-y plane and the lens in the z direction. Alternatively, the sample can be kept fixed and the lens has all the three-degree of freedom (x-y-z) on its own. Any other arrangement is also possible.

The laser light is reflected by a polarization beam splitter PBS, i.e. a polarization dependent reflector, and is passed through a quarter wave plate $\lambda/4$ and a first band pass filter BP1.

A dichroic beam splitter DBS, i.e. a wavelength dependent reflector, directs the laser light to the excitation lens 16.

The induced fluorescence, (as a result of the excitation light focused into the sample) is collected by a collection lens, which in this example is the same component as the excitation lens 16, and is directed toward a detector 18.

Any reflected unabsorbed laser light is reflected again by the beam splitter DBS, whereas the fluorescence luminance is passed through the beam splitter DBS. A second band pass filter BP2 provides further filtering, and the light is then focused on the detector 18 by an imaging lens L2 which images the sample onto the detector.

Many different types of detector can be used such as a photon tube multiplier, avalanche photon detector, CCD detector or photodiode detector.

For confocal imaging, the excitation volume is kept to a minimum, ideally to the diffraction limited spot that the excitation lens 16 can create. A typical confocal volume is in the order of a cubic micron, depending on the strength (numerical aperture, NA) of the excitation lens 16. The fluorescence created in this volume is collected by the collection lens and is imaged on the detector. In a confocal method, the focal point is confocal with a point in the detection path. At this point in the detection path, a small pinhole is typically placed to filter out any light coming from a location other than the focal point.

The light passing the pinhole is directed toward the detector. It is possible for the detector itself to play the role of the pinhole, with the restriction that the lateral size of the detector has to match the size of the focal point scaled by the focal length of the collection lens 16 divided by the focal length of the imaging lens L2.

This confocal mode is best suited to investigate a surface immobilization assay, as the result of an endpoint bio-experiment. The surface is scanned to analyze the full sample.

The lateral dimensions of the detector are designed taking into account the fields of the collection lens 16 and the imaging lens L2.

A control arrangement 19 keeps the focus of the objective lens precisely at the inner surface of the analytical device which is in contact with the analyte, while scanning the same surface. The focus of the objective lens can also be offset on purpose.

This invention can be applied to the diffraction spot analysis apparatus explained with reference to FIG. 1.

However, It has also been proposed to illuminate a sample using a number of spots or even a complete line in parallel. This enables the time of the analysis to be reduced. An excitation beam in the form of a confocal line, rather than a confocal spot can thus be used.

The invention will be described with reference to a confocal line excitation system. The basic system is shown in FIG. 2.

Figure 2:
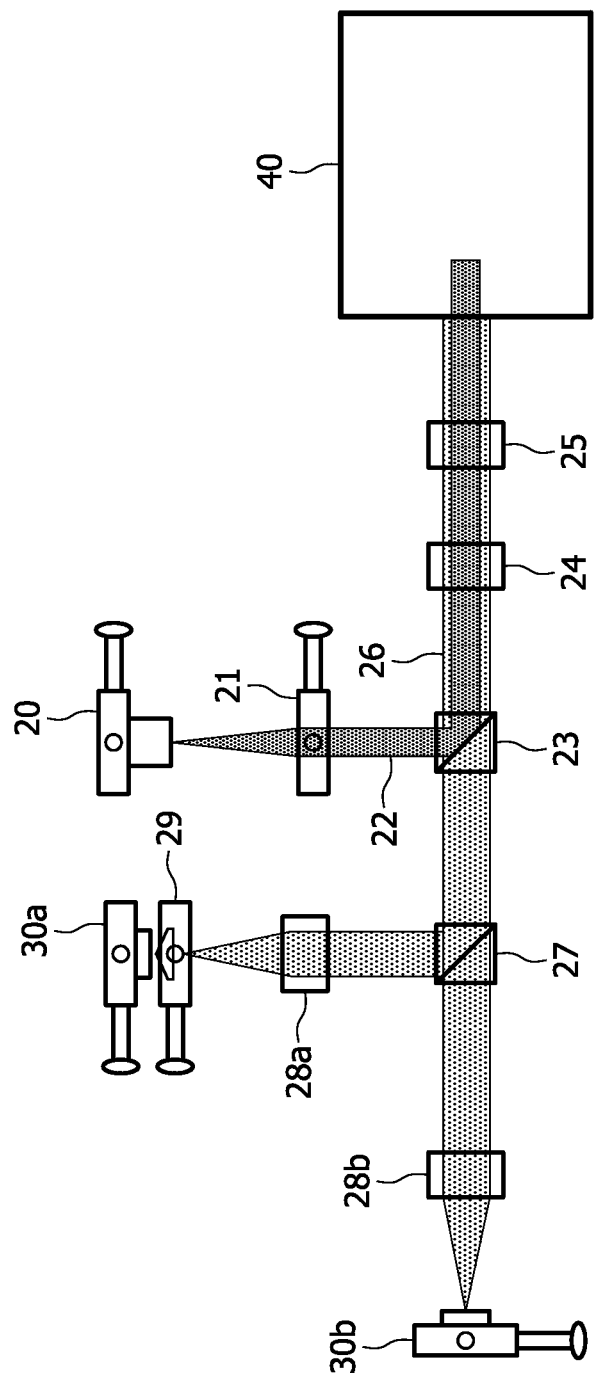
FIG. 2 shows an example of confocal scanner using an optical scanning apparatus of the invention.

The example of FIG. 2 uses a split optics design, in which part of the optics is fixed and part of the optics is moved.

The basic function of the system is the same as explained with reference to FIG. 1. Thus, light from a laser 20 is collimated with a lens 21 to form a parallel excitation beam 22. This light is polarized such that it is reflected by a polarizing beam splitter 23. The light then passes through a ¼λ-plate 24, resulting in circular polarized light. Next the light passes through a bandpass filter 25 to reject any unwanted wavelengths from the excitation light. The light is then passed on to a scanner 40.

The scanner 40 implements the confocal line scanning, and also implements the simplified detector arrangement of the invention.

Figure 3:
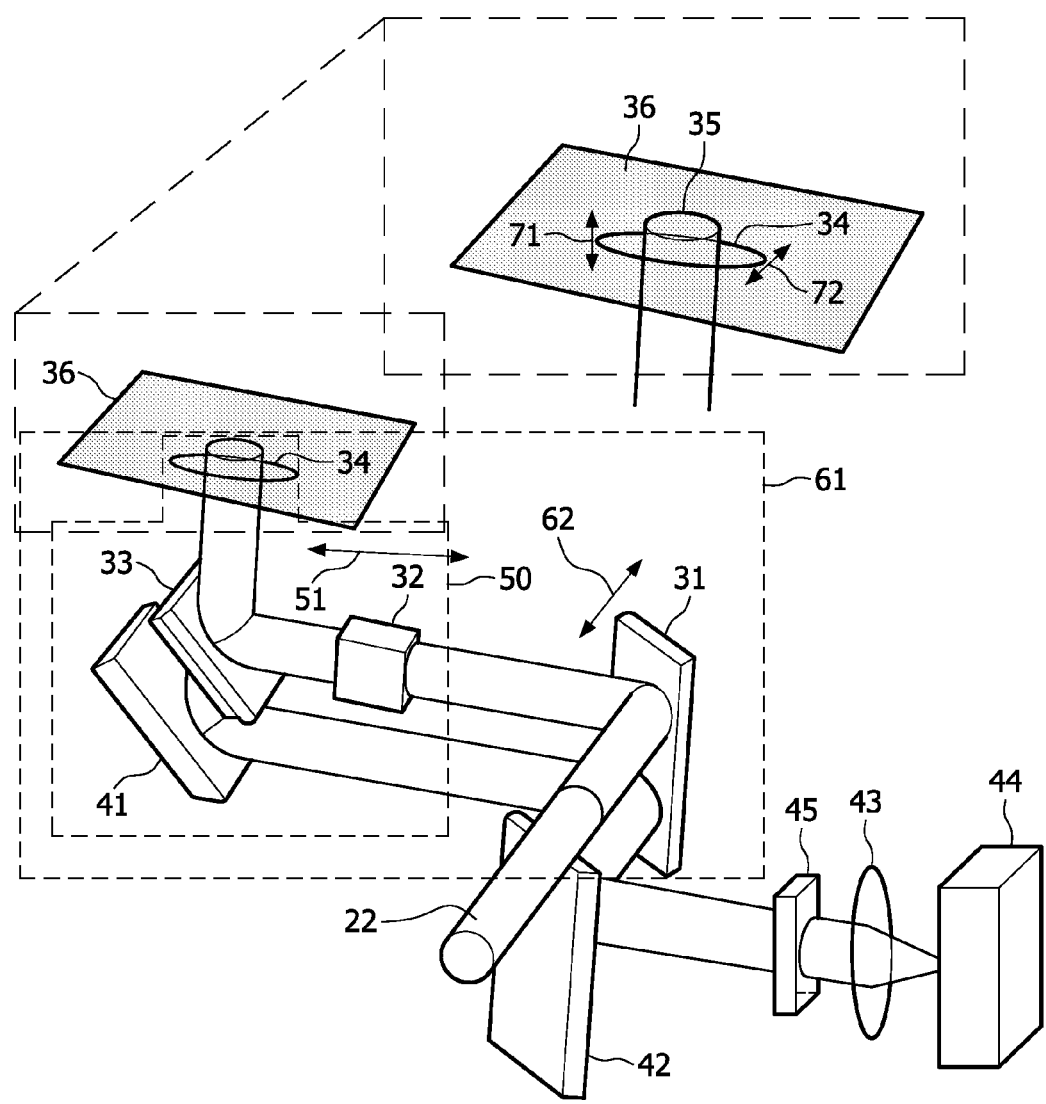
FIG. 3 shows the detector used in the system of FIG. 2 in more detail.

FIG. 3 shows the scanner 40 in more detail, and shows the light paths through the scanner.

The incoming light 22 passes over a mirror 42 and is reflected by a mirror 31. A cylindrical lens 32 retracts the light in one direction, in order to provide the conversion to a confocal line. The light is then reflected by a dichroic mirror 33 and focused by the objective lens 34 on the sample 36.

Due to the divergence in one direction implemented by the lens 32, the focus will result in a line 35. The fluorescent molecules are excited by this excitation light.

The fluorescence light has a longer wavelength, and as in the example of FIG. 1, this enables the fluorescence light to follow a different path to the excitation path, by means of wavelength-dependent components.

The objective lens 34 can be moved in a depth direction 71 (perpendicularly towards or away from the sample) to allow focusing on the sample. In addition, by moving the lens 34 in direction 72, the line on the sample 35 can be moved in a direction perpendicular to the long axis of the focus line 72. Thus, single axis scanning in direction 72 enables excitation of a 2D area of the sample.

Both reflected light as well as fluorescence is collected with the objective lens 34. The reflected light is reflected again by the dichroic mirror 33 and passes again through the cylinder lens 32. This results in a slightly converging beam in one direction. The light is then reflected by mirror 31 and enters the optics again as beam 26 in FIG. 2.

With reference to FIG. 2. this light then passes again through the band pass filter 25 and the ¼λ-plate 24. Since the light has now passed twice though the ¼λ-plate, it is rotated over 90 degrees with respect to the original laser light and is thus now transmitted by the polarizing beam splitter 23.

Part of the reflected light is reflected by a beam splitter 27. This is focused by a lens 28a through a Foucault prism 29 on to a split detector 30a. The signal from this detector is used for the automatic focusing of the light on to the sample 36.

Part of the light that impinged on the beam splitter 27 is transmitted and is focused by a lens 28b on split detector 30b. The signal of this split detector is used to allow the tracking of the features on the sample 36.

Returning to FIG. 3, the fluorescent light is transmitted by the dichroic mirror 33 and is reflected by mirror 41. This light is then reflected below the incoming light on mirror 31 and is therefore reflected by mirror 42. A filter 45 is used to further separate the fluorescence light from the excitation light. A lens 43 is used to project the light on the detector 44. The cylinder lens 32 resulted in the illumination of a line on the sample 36, and the image on the detector 44 is a projection of this line.

It can be seen that the scanner 40 implements two optical paths. One is a path for the collection light between the sample 36 and the detector 44. This comprises transmission through the wavelength dependent reflector 33, reflection at a first reflector (the mirror 41), reflection at a second reflector (the mirror 31) and reflection at a third reflector (the mirror 42). The other path is a light source light path between an input to the reflector arrangement 23 and the sample 36. This comprises reflection at the second reflector (the mirror 31), and reflection at the wavelength dependent reflector 33. This second path misses the third reflector (the mirror 42) and the first reflector (the mirror 41) but includes the cylindrical lens 32.

The components shown in the box labeled as 61 can be considered together to define a reflector arrangement. The two mirrors 31 and 41 reflect the collected light in perpendicular planes. By this is meant that the input and output light beam for the mirror 41 is in a first plane which includes the normal to the surface of the mirror. The input and output light beam for the mirror 31 is in a second plane which includes the normal to the surface of the mirror, and the first and second planes are perpendicular to each other. In this way, a 3D Z shaped path (with right angled corners) is defined as can be seen in FIG. 3. This means each mirror can be adjusted independently, to provide scanning of the line beam along one axis. Furthermore, it means the position of the beam with respect to the mirror 42 is static even when the line beam is scanned across the sample.

To build up an image of the sample, the elements in selection 50 (the lens 34, cylinder lines 32, reflector 41 and wavelength dependent reflector 33) are moved in direction shown by arrow 51. This direction is perpendicular to the direction of the line that is generated by the cylindrical lens 32, and is parallel with the path of the collection light reflected by the mirror 41, i.e. parallel with the path of the excitation light incident on the wavelength dependent reflector 33. This allows scanning in a first direction along the axis of the excitation line.

To scan in the perpendicular direction, the elements of selection 50 are moved together with mirror 31 in the direction shown as 62. This is parallel with the incoming excitation light to the mirror 31, i.e. parallel with the collection light reflected by the mirror 31.

This arrangement ensures that the image on the detector 44 and the light on the other optical components depicted in FIG. 2 does not shift while measuring the different positions on the sample. During scanning, the detector is read out with a certain integration time/bandwidth.

Thus, the reflector arrangement enables scanning of the line beam over the sample of interest. In addition, shared optical components ensure that the beam provided to the detector 44 remains static.

This implementation of the invention thus enables the use of a parallel excitation approach, in combination with a simple photodiode as the detector 44. The shape of the active area of the detector is then matched to that of the illumination spot, and this remains static.

For confocal operation, it is important to match the shape and size of the photodiode of the detector to the size of the excitation line. This can be seen from FIG. 4 which depicts the general principle of confocal detection by showing the optical path of a confocal microscope.

Figure 4A:
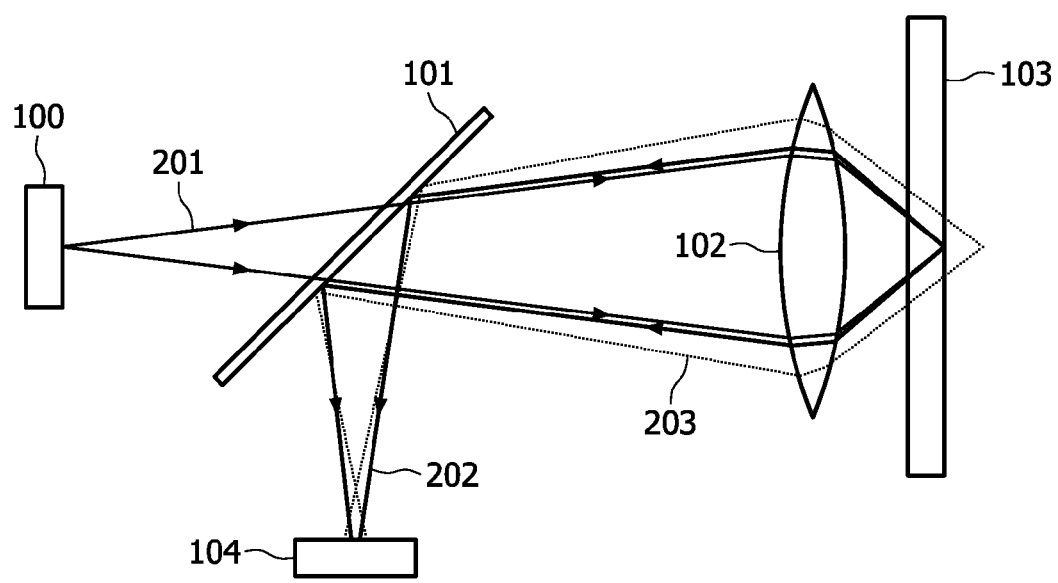
FIG. 4 is used to explain the requirements for confocal scanning.

As shown in FIG. 4a, the light 201 from a laser 100 is focused by a lens 102 on the substrate 103. The fluorescent light 202 that is generated in the excitation focus is imaged by lens 102 via a dichroic mirror 101 on a detector 104.

Figure 4B:
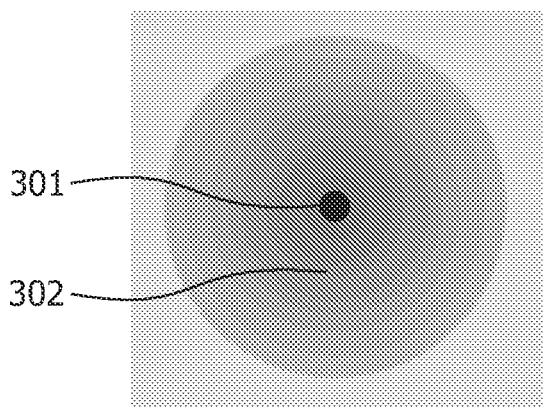
Figure 4C:
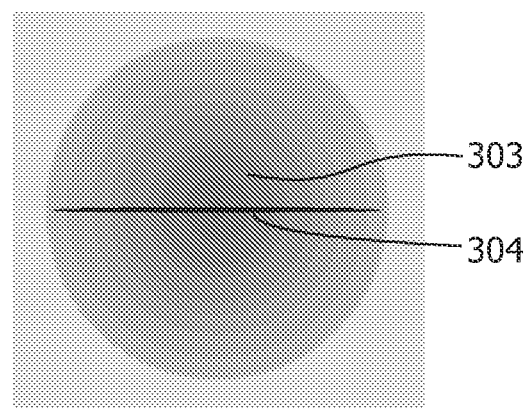

FIG. 4b depicts the light in the detector plane. The in-focus light is focused to a small spot 301, and the out-of-focus contribution 203 results in a larger spot 302 on the detector plane. When a line is used to illuminate the sample the resulting fluorescence will also form a narrow line in the detector plane 304, this situation is depicted in FIG. 4c. Again the fluorescence generated outside the focal plane of lens (102) will form a larger spot in the detector plane 303.

To reject the background it is thus important to ensure that the size and orientation of the detector is matched to fluorescence line in the detector plane. The excitation line on the substrate can be approximately 100 μm×1 μm. If a magnification of 10× is used in the detection path, the fluorescence will form a stripe of approximately 1 mm×10 μm on the detector.

It is in principle possible to fabricate a diode with an active area of this size. The advantage of this is that the active area is rather small, resulting in a reduced dark current. However, when it is not feasible to design a specific diode it is possible to use a diode where part of the active area is masked of. This can be done by either adding a (metallic) mask directly on the diode or by placing a screen with a narrow slit in front of the diode. In that case, the focus of the lens 43 (in FIG. 3) should coincide with the opening of the slit; the diode can then be placed at an arbitrary distance behind the slit as long as all the light passing through the slit is collected.

The detected signal is preferably read out using an integrating amplifier. This is preferred as a result of the low current levels involved. For example, the amount of fluorescent light that is generated may be around 200 fW at 700 nm. This will result in a current signal of around ~100 fA.

Figure 5:
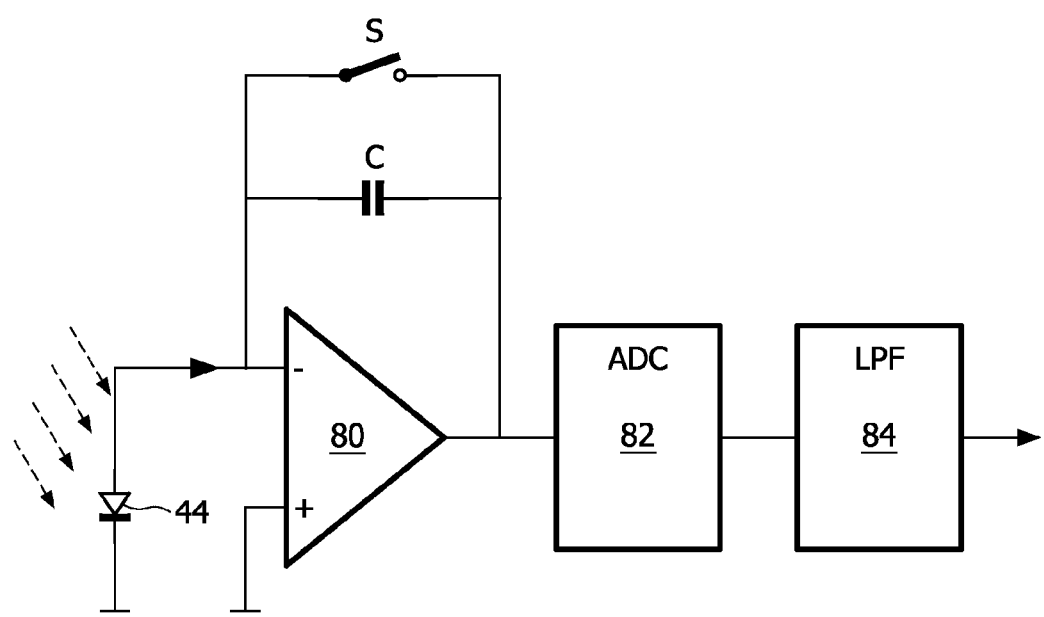
FIG. 5 shows an example of detector amplifier which can be used.

This current can in principal be converted to a voltage with a trans-impedance amplifier. However, the problem with such an amplifier is that a large amount of noise is added by the large resistor required. A better method is the use of an integrating operational amplifier as shown in FIG. 5, with a small integrating capacitor C (for example 100 pF). This converts the current into a voltage that can then be measured with a fast and precise Analogue-to-Digital converter.

FIG. 6 shows various waveforms appearing in the circuit of FIG. 5, based on a simulation in which three regions are defined on the sample surface, which show a maximum signal intensity of 100 fA and a diameter of 150 μm. During the simulation, the sample was scanned with a velocity of 1 mm/s.

Figure 6A:
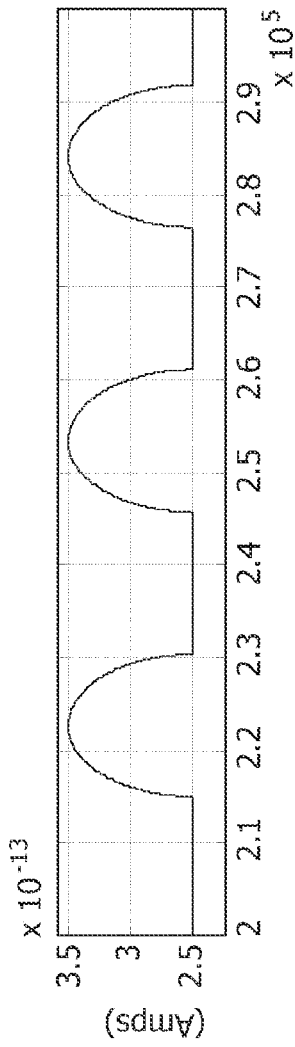
FIG. 6 shows plots of signals at different points in the circuit of FIG. 5.

The circuit of FIG. 5 comprises the detector 44 for receiving photons from the excited fluorescence. The resulting input current is shown in FIG. 6a.

Figure 6B:
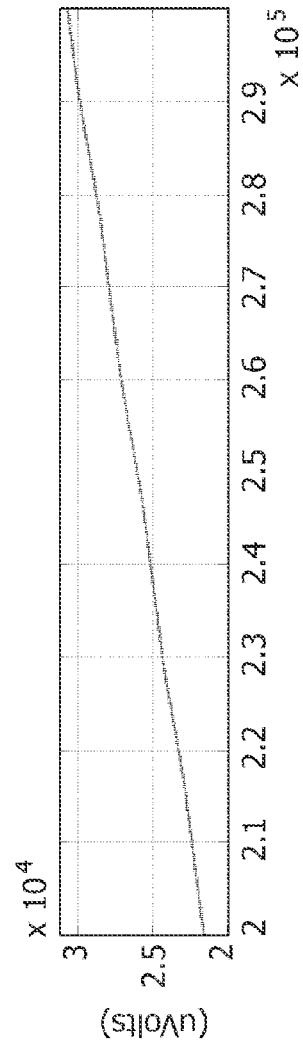

The opamp is shown as 80 with a capacitor C and switch S in parallel in a feedback path to the inverting input. These can be on-chip components of an opamp package. The ADC 82 provides as output a sampled integrator output as shown in FIG. 6b. In the simulation, noise from a real measurement was added to this signal.

Figure 6C:
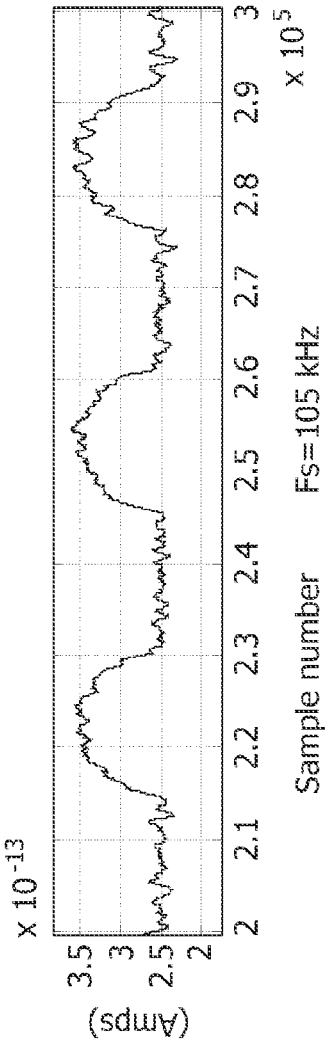

After serial processing, low pass filtering (at 60 Hz and 120 Hz) and differentiation with DeltaT=7.3 msec in block 84, the output shown in FIG. 6c results. The different spots can be clearly distinguished from the background.

The invention can be used in the field of compact optical biosensors in particular for the use in a point of care testing setting. Such bio sensors can be used to detect different types of molecules such as proteins, DNA/RNA and small molecules in the field of molecular diagnostics.

The optical system can be based on the optics of a standard CD/DVD player/writer.

In the example above, a lens 34 is used both for the excitation light and the fluorescence light, and it can also be used for focus and tracking signals. Separate lenses may be used for the excitation light and the fluorescence light, for example with non-normal directions of illumination, or with operation in a transmissive mode.

The invention is of particular interest for confocal scanning/line scanning However, more generally, the invention relates to the scanning of an optical collection arrangement over a sample, with the collected signal routed to the same position on a static detector, so that the detector aperture can be matched to the size of the scanned region of the sample. This concept can be used for fluorescence detection, in which excitation light is provided to the sample, but it can also be used only for light collection where no excitation is required, for example for detecting luminescence.

The scanning in the example described above can be in two directions. However, scanning in only one direction may be sufficient, particularly when a confocal line collection region is used. The invention can also be applied to systems which scan a confocal collection spot over a sample.

The preferred applications of the invention are in the field of molecular diagnostics, clinical diagnostics, point-of-care diagnostics, advanced bio-molecular diagnostic research and optical bio sensors, in particular related to DNA detection in combination with amplification methods, such as PCR, q-PCR, etc. The invention can also be used as a line scanner for imaging cells and/or tissue for example for pathology purposes. The can also be used for detection in an immunoassay to detect proteins.

The detailed example above is only one example. A large number of other designs are possible, such as a system where the complete optics is scanned or where the sample is scanned with respect to the optics.

The example above uses a cylinder lens for generating the line-shaped excitation light and collection region (in fact, the line is the result of the combined transfer functions of the cylinder lens and the sample lens). A phase plate can be used instead of a cylindrical lens.

Various other modifications will be apparent to those skilled in the art.

The invention claimed is:

1. An optical system for detecting light from a 2D area of a sample, comprising:
    a collection lens for collecting light from a collection region of the sample, the collection lens being movable relative to the sample;
    a light detector which is in use positionally fixed with respect to the sample; and
    a reflector arrangement comprising moveable components for directing collected light to the detector, the reflector arrangement further configured to direct collected light over a same light path as input into the reflector arrangement to provide optical feedback for adjusting incident light,
    wherein the collection lens and the movable components are configurable to define different collection regions, and wherein the movement of the components effects a direction of the light from the collection region to a substantially unchanged area of the light detector.

2. A system as claimed in claim 1, wherein the reflector arrangement comprises first and second reflectors which reflect the collected light in perpendicular planes, and a third reflector which directs the collected light output from the second reflector to the detector.

3. A system as claimed in claim 2, wherein the first and second reflectors comprise movable components, movable along the axis of the reflected collected light.

4. A system as claimed in claim 1, further comprising an illumination system for illuminating the sample, the illumination system comprising:
   a light source; and
   an arrangement for directing the light source output to the reflector arrangement, wherein the reflector arrangement directs the light source output to the sample.

5. A system as claimed in claim 4, wherein the reflector arrangement comprises first and second reflectors which reflect the collected light in perpendicular planes, a third reflector which directs the collected light output from the second reflector to the detector, and a wavelength dependent reflector, wherein:
   a first, collection light path between the sample and the detector comprises transmission through the wavelength dependent reflector, reflection at the first reflector, reflection at the second reflector and reflection at the third reflector; and
   a second, light source light path between an input to the reflector arrangement and the sample comprises reflection at the second reflector, and reflection at the wavelength dependent reflector.

6. A system as claimed in claim 5, wherein the second path misses the third reflector and the first reflector.

7. A system as claimed in claim 5, wherein the reflector arrangement further comprises a cylindrical lens or phase plate only in the second, light source path.

8. A system as claimed in claim 5, comprising a fluorescence detection system, wherein the illumination system is for excitation of the sample to generate fluorescence.

9. A system as claimed in claim 1, wherein the collection region comprises a line with diffraction limited width.

10. A system as claimed in claim 1, wherein the light sensitive area of the detector is matched to the size and shape of the illumination provided to the detector by the reflector arrangement.

11. A system as claimed in claim 1, wherein the detector comprises a single light sensitive area.

12. A system as claimed in claim 11, wherein the detector comprises a photodiode.

13. A system as claimed in claim 1, wherein the detector comprises an imaging lens which focuses onto the detection surface.

14. A method of collecting light from a sample, comprising:
   scanning a collection lens to collect light from a succession of collection regions of the sample, the collection lens being movable relative to the sample; and
   using a reflector arrangement comprising movable components to direct collected light to a detector, the reflector arrangement further configured to direct collected light over a same light path as input into the reflector arrangement to provide optical feedback for adjusting incident light,
   wherein the method comprises configuring the collection lens and the movable components to define the different collection regions, and wherein the movement of the components effects a direction of the light from the collection region to a substantially unchanged area of the light detector.

15. A method of measuring the fluorescence from a sample, comprising:
   scanning an optical signal across the sample thereby providing excitation radiation to the collection regions; and
   collecting light emitted from the analysis region of the sample by excitation-induced fluorescence using the method of claim 14; and
   detecting the collected light.

* * * * *